United States Patent
Sage et al.

(10) Patent No.: US 9,427,571 B2
(45) Date of Patent: Aug. 30, 2016

(54) DYNAMIC COIL FOR IMPLANTABLE STIMULATION LEADS

(75) Inventors: Shahn S. Sage, Andover, MN (US); Tom Walch, Centerville, MN (US); Martin T. Steele, Sr., Otsego, MN (US); John Swoyer, Blaine, MN (US)

(73) Assignee: Nuvectra Corporation, Plano, TX (US)

( * ) Notice: Subject to any disclaimer, the term of this patent is extended or adjusted under 35 U.S.C. 154(b) by 614 days.

(21) Appl. No.: 13/538,074

(22) Filed: Jun. 29, 2012

(65) Prior Publication Data

US 2014/0005599 A1    Jan. 2, 2014

(51) Int. Cl.
*A61N 1/05* (2006.01)
*A61N 1/36* (2006.01)

(52) U.S. Cl.
CPC .............. *A61N 1/0551* (2013.01); *A61N 1/056* (2013.01); *A61N 1/3605* (2013.01); *Y10T 29/49117* (2015.01)

(58) Field of Classification Search
CPC ....... A61N 1/056; A61N 1/0551; A61N 1/05; A61N 1/0509; A61N 1/0558; A61N 1/3605; A61N 2001/0578; A61N 2001/0585
USPC ........................................ 604/93.01; 607/116
See application file for complete search history.

(56) References Cited

U.S. PATENT DOCUMENTS

| | | | |
|---|---|---|---|
| 1,978,591 A | 10/1934 | Meiwald | |
| 2,013,211 A | 9/1935 | Herkenberg | |
| 4,559,951 A * | 12/1985 | Dahl et al. | 600/374 |
| 5,003,992 A * | 4/1991 | Holleman et al. | 607/120 |
| 5,683,445 A * | 11/1997 | Swoyer | 607/125 |
| 5,800,496 A * | 9/1998 | Swoyer et al. | 607/122 |
| 5,954,759 A * | 9/1999 | Swoyer | A61N 1/156 607/122 |
| 6,720,497 B1 * | 4/2004 | Barsne | A61N 1/056 174/102 R |
| 6,741,893 B2 | 5/2004 | Smits | |
| 6,823,217 B2 | 11/2004 | Rutten et al. | |
| 7,957,818 B2 * | 6/2011 | Swoyer | 607/116 |
| 8,543,223 B2 * | 9/2013 | Sage et al. | 607/116 |
| 2002/0103522 A1 * | 8/2002 | Swoyer et al. | 607/116 |
| 2010/0114277 A1 * | 5/2010 | Zhao | A61N 1/056 607/116 |
| 2014/0005599 A1 * | 1/2014 | Sage et al. | 604/93.01 |

* cited by examiner

*Primary Examiner* — Nathan R Price
*Assistant Examiner* — Anh Bui
(74) *Attorney, Agent, or Firm* — Haynes and Boone, LLP; Eric Q. Li

(57) ABSTRACT

An implantable biomedical conductor assembly is configured for at least partial insertion in a living body. The implantable conductor assembly includes an inner tubular structure and an outer tubular structure generally surrounding the inner tubular structures such that a gap of less than about 0.030 inches exists therebetween. A dynamic coil is located in the gap. The dynamic coil includes a plurality of insulated conductors that are coiled generally at or below a yield point. The insulated conductors are permitted to expand within the gap to engage an inner surface of the outer tubular structure in an expanded coiled configuration. At least one mechanical restraint at each of a distal end and a proximal end retains the dynamic coil in the tubular structures. Free ends of the insulated conductors extend beyond the proximal and distal ends to facilitate attachment to electrodes and connectors.

21 Claims, 11 Drawing Sheets

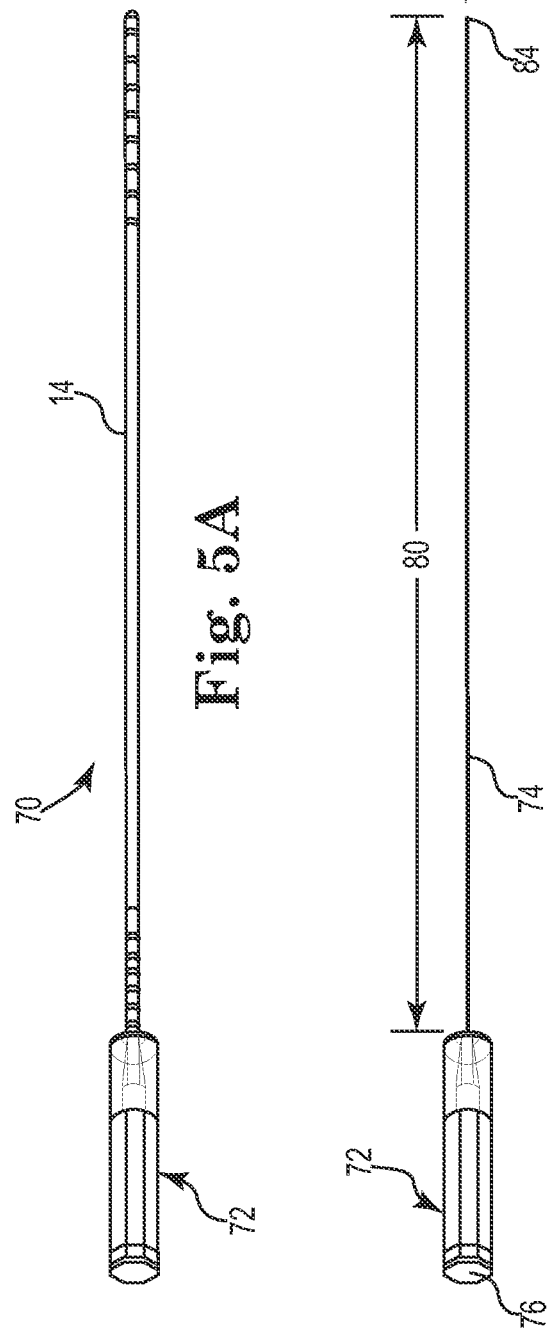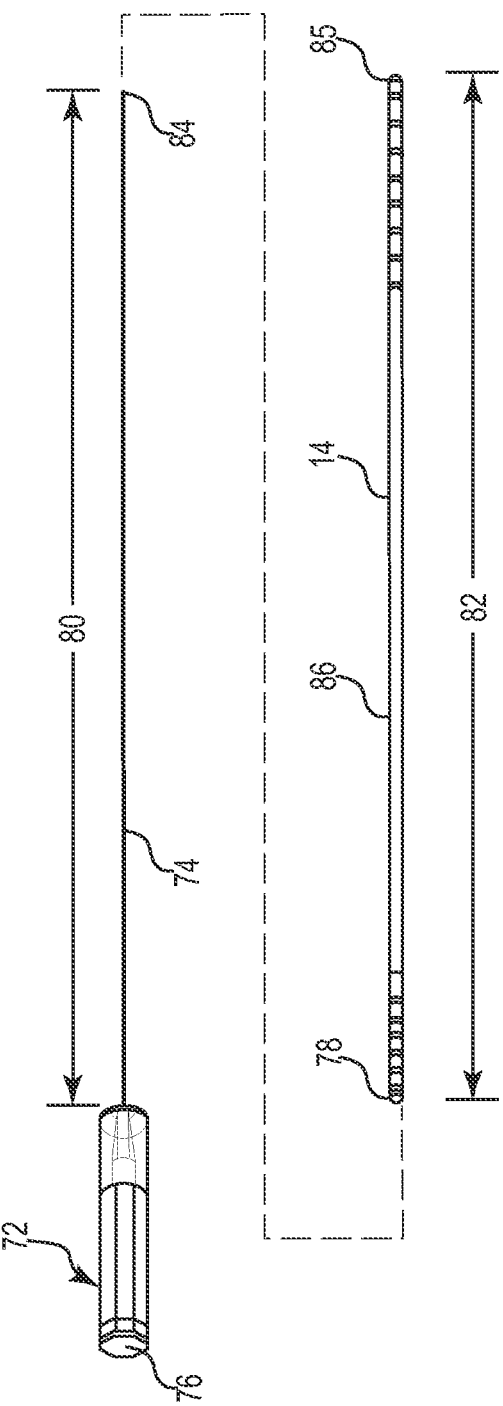

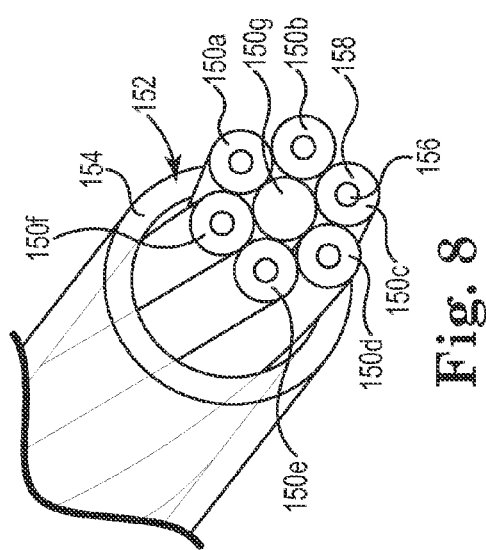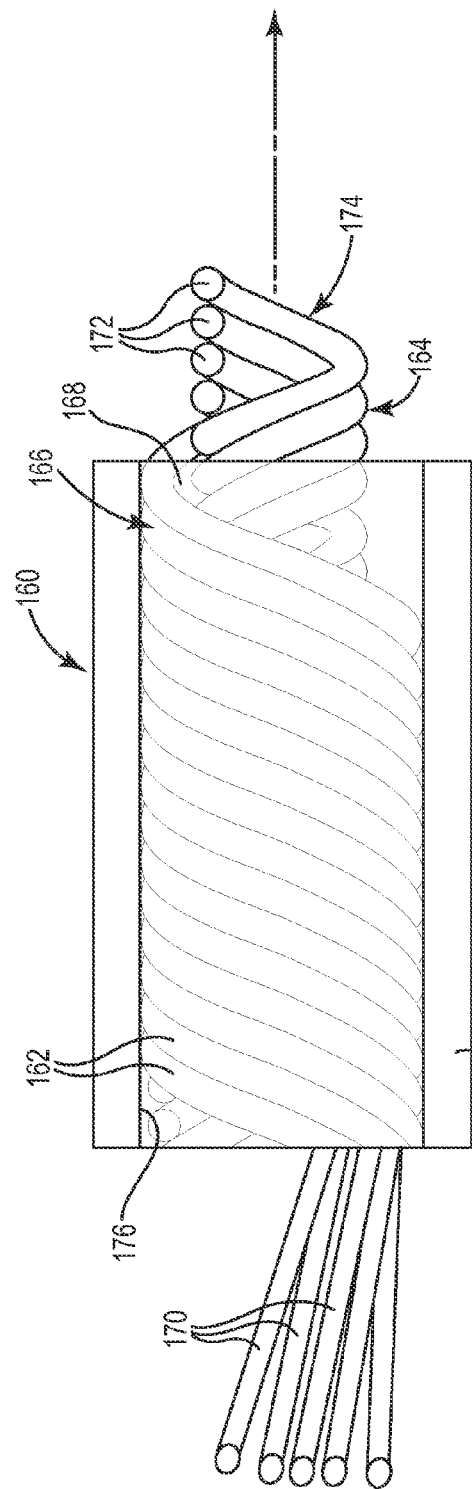

DYNAMIC COIL FOR IMPLANTABLE STIMULATION LEADS

FIELD

The present disclosure is directed to a biomedical implantable conductor assembly with a dynamic coil formed at or below the yield point of the insulated conductors. The present dynamic coil can have sixteen or more discrete conductors, yet elongates like a conventional coil when loaded axially. The present dynamic coil also has superior flex fatigue properties over conventional leads.

BACKGROUND

The human body imposes stringent requirements on electrical conductors that are implanted within it. Leads inserted in a living body that form a part of a stimulation and/or measuring/sensing or drug delivery device are subjected to almost continuous flexure during body movement. Also, a living body constitutes a site that is chemically and biologically hostile to anything that invades it. Consequently, leads ideally have good deformability, particularly bending ability, high fatigue resistance, corrosion resistance, and a high degree of electric conductance.

U.S. Pat. No. 4,640,983 (Comte) discloses a lead body having at least one spiral which is formed from at least one conductor. Each conductor consists of wires that are stranded together to form a bundle. The wires belonging to a conductor can all consist of the same material or of different materials, one of which has a large breaking strength and the other one having high electric conductivity. One embodiment discloses inner and outer coils wound in the same direction and separated by an insulating sheath.

U.S. Pat. No. 5,483,022 (Mar) discloses a lead body having at least one helical coil formed from at least one electrical cable. Each cable is formed from several wires twisted in a ropelike configuration. Each wire is a composite of a core of a highly conductive material and a coveting of a strong and biocompatible material, with all adjacent wires belonging to the same cable in un-insulated contact with each other. One embodiment discloses inner and outer coils wound in the same direction and separated by an insulating sheath.

U.S. Pat. No. 6,978,185 (Osypka) discloses a lead body having electrically active and inactive elements helically wound together. The active elements are separated from each other by the inactive elements. One embodiment discloses inner and outer coils wound in opposite directions and separated by an insulating sheath.

When winding coiled lead bodies the conductors or cables are typically strained beyond the yield point so the conductors or cables retain a coiled configuration. When the winding force is removed, the conductors or cable provide a self-supporting coil.

This construction method, however, limits the number of individual conductors in a given lead body. First, current multi-conductor coils permit essentially zero elongation. Second, the flex fatigue life of the conductors is reduced if too many conductors are located in different planes for a given coil diameter. As a result, lead bodies are typically limited to an inner coil with about four conductors and an outer coil with four to eight conductors.

BRIEF SUMMARY

The present disclosure is directed to a biomedical implantable conductor assembly with a dynamic coil formed at or below the yield point of the insulated conductors. The dynamic coil can have sixteen or more discrete conductors, yet elongates like a coil when loaded axially. The present implantable conductor assembly has similar flex fatigue properties as a straight conductor or cable.

The present implantable biomedical conductor assembly is configured for at least partial insertion in a living body. The implantable conductor assembly includes an inner tubular structure and an outer tubular structure generally surrounding the inner tubular structures such that a gap of less than about 0.030 inches exists there between. A dynamic coil is located in the gap. The dynamic coil includes a plurality of insulated conductors that are coiled generally at or below a yield point. The dynamic coil is permitted to expand within the gap to engage an inner surface of the outer tubular structure in an expanded coiled configuration. At least one mechanical restraint at each of a distal end and a proximal end retains the dynamic coil in the tubular structures. Free ends of the insulated conductors extend beyond the proximal and distal ends to facilitate attachment to electrodes and connectors.

At least a portion of the dynamic coil will unravel if one or more of the mechanical restraints are removed. Any remaining coils in the insulated conductors will a diameter greater than a diameter of the dynamic coil.

The mechanical restraints can be attachment locations that secure the insulated conductors to at least one of the inner or outer tubular structures near the proximal and distal ends. In another embodiment, the mechanical restraints can be free ends of the insulated conductors attached to at least one of the electrodes or the connectors.

The coiled configuration preferably includes a plurality of insulated conductors having portions thereof arranged in a single plane. In one embodiment, the expanded coiled configuration includes up to twelve insulated conductors and the implantable conduct assembly exhibits a percent elongation in a range between about 10 percent to about 35 percent. In another embodiment, the implantable conductor assembly exhibits a percent elongation in a range between about 10 percent to about 25 percent.

The implantable conductor assembly preferably has an outside diameter of less than about 0.080 inches, and more preferably, less than about 0.060 inches. The implantable conductor assembly meets the bending radius and flex fatigue requirements set forth in European Standard EN 45502-2-1: 2003, Section 23.3. The inner tubular structure can be one of a stylet coil, a braided structure, extruded tube, or a combination thereof. The inner tubular structure preferably includes a lumen.

The implantable conductor assembly preferably includes at least one electrical connector assembly coupled to the proximal end of the tubular structures and at least one electrode assembly coupled to the distal end of the tubular structures. The implantable conductor assembly can form a portion of a medical electrical lead or a fluid delivery device.

The present disclosure is also directed to an implantable biomedical conductor including a tubular structure comprising a lumen. A dynamic coil is located in the lumen. The dynamic coil includes a plurality of insulated conductors that are coiled generally at or below a yield point. The dynamic coil is permitted to expand within the lumen to engage an inner surface of the lumen in an expanded coiled configuration. At least one mechanical restraint at each of a distal end and a proximal end retains the dynamic coil in the lumen. Free ends of the insulated conductors extend beyond the proximal and distal ends to facilitate attachment to electrodes and connectors.

The present disclosure is also directed to a therapy delivery element including the present dynamic coil. A plurality of electrical connectors is coupled with the insulated conductors at the proximal end of the tubing and a plurality of electrodes is coupled with the insulated conductors at the distal end of the tubing. The therapy delivery element preferably includes a stylet configured to be located in a lumen formed within the dynamic coil.

The present disclosure is also directed to a method of making a therapy delivery element configured for at least partial insertion in a living body. The method includes positioning an inner tubular structure within an outer tubular structure such that a gap exists there between. A dynamic coil is formed including a plurality of insulated conductors retained in a coiled configuration generally at or below a yield point of the insulated conduct. The dynamic coil is located in the gap. The insulated conductors are secured in the coiled configuration by at least one mechanical restraint located at each of a distal end and a proximal end of the tubular structures. The dynamic coil is permitted to expand within the gap to engage an inner surface of the outer tubular structure in an expanded coiled configuration. Free ends of the insulated conductors are permitted to extend beyond distal and proximal ends of the inner and outer tubular structures.

The method includes attaching the insulated conductors to at least one of the inner or outer tubular structures near the proximal and distal ends. The free ends of the insulated conductors at the distal end are electrically coupled to an electrical contact assembly and at the proximal end to an electrode assembly.

The plurality of insulated conductors is preferably arranged in a single plane. The inner tubular structure can be selected from one of a stylet coil, a braided structure, extruded tube, or a combination thereof. A stylet wire is optionally inserted in a lumen extending through the dynamic coil.

BRIEF DESCRIPTION OF THE DRAWINGS

FIG. 5A is a schematic illustration of a stylet-lead assembly in accordance with an embodiment of the present disclosure.

FIG. 5B is an exploded view of the stylet-lead assembly of FIG. 5A.

FIG. 8 is a perspective view of an insulated conductor in accordance with an embodiment of the present disclosure.

FIG. 9 illustrates an alternate dynamic coil with a coiled core in accordance with an embodiment of the present disclosure.

The drawings are not necessarily to scale. Like numbers refer to like parts or steps throughout the drawings.

DETAILED DESCRIPTION OF SOME EMBODIMENTS

The description that follows relates to a spinal cord stimulation (SCS) system. However, it is to be understood that the while the present disclosure lends itself well to applications in SCS, the disclosure in its broadest aspects is not so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

In another embodiment, one or more of the therapy delivery elements may be a fluid or drug delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be a medical electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, and any combination thereof. "Target tissue site" refers generally to the target site for implantation of a therapy delivery element, regardless of the type of therapy.

Figure 1:
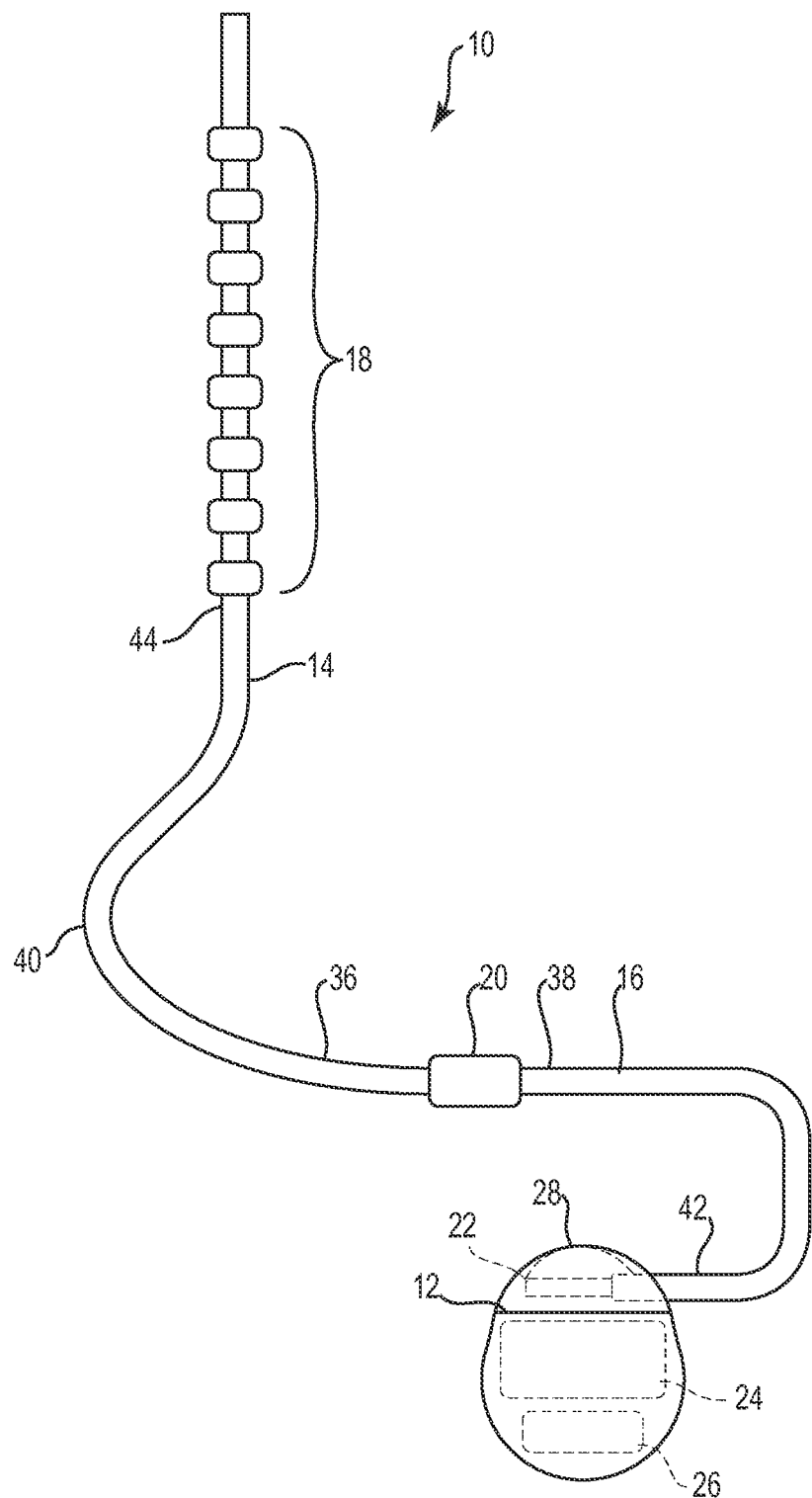
FIG. 1 is a schematic illustration of a therapy delivery system.

FIG. 1 illustrates a generalized therapy delivery system 10 that may be used in spinal cord stimulation (SCS), as well as in other stimulation applications. The therapy delivery system 10 generally includes an implantable pulse generator 12 ("IPG") ("IPG"), an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10.

The therapy delivery element 14 includes lead body 40 having a proximal end 36 and a distal end 44. The lead body 40 typically has a diameter ranging between about 0.03 inches to about 0.07 inches and a length ranging between about 30 cm to about 90 cm for spinal cord stimulation applications. The lead body 40 may include a suitable electrically insulative coating, such as, a polymeric material (e.g., polyurethane or silicone).

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector 22 associated with housing 28. Alternatively, the proximal end 36 of the therapy delivery element 14 can be electrically coupled directly to the connector 22.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 protected from the body tissue and fluids. The connector 22 is disposed in a portion of the housing 28 that is, at least initially, not sealed. The connector 22 carries a plurality of contacts that electrically couple with respective terminals at proximal ends of the therapy delivery element 14 or extension lead 16. Electrical conductors extend from the connector 22 and connect to the electronic subassembly 24.

Figure 2:
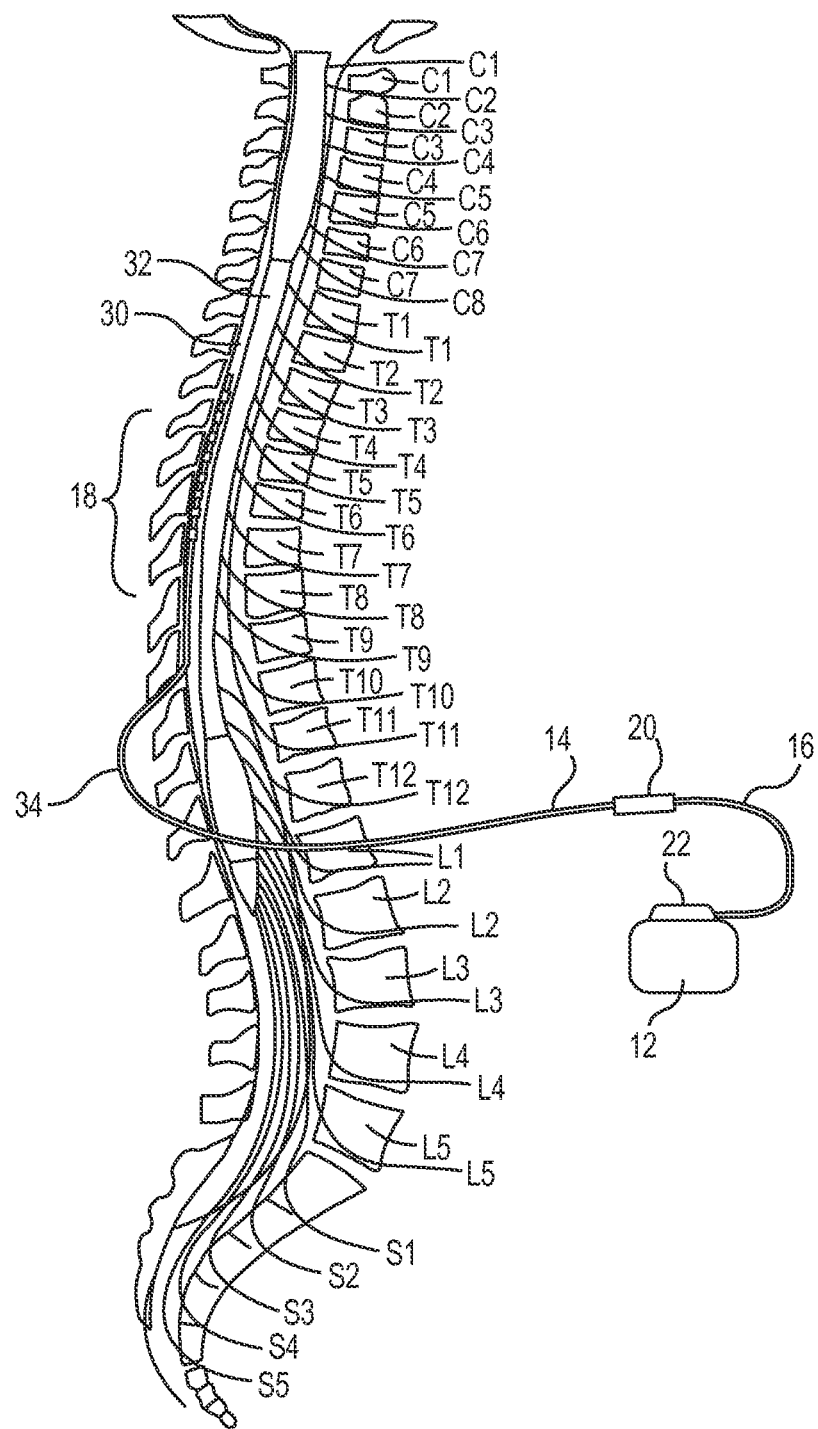
FIG. 2 is a schematic illustration of an environment for a therapy delivery system in accordance with an embodiment of the present disclosure.

FIG. 2 illustrates the therapy delivery element 14 implanted in the epidural space 30 of a patient in close proximity to the dura, the outer layer that surrounds the spinal cord 32, to deliver the intended therapeutic effects of spinal cord electrical stimulation. The target stimulation sites may be anywhere along the spinal cord 32, such as for example proximate the sacral nerves.

Figure 3:
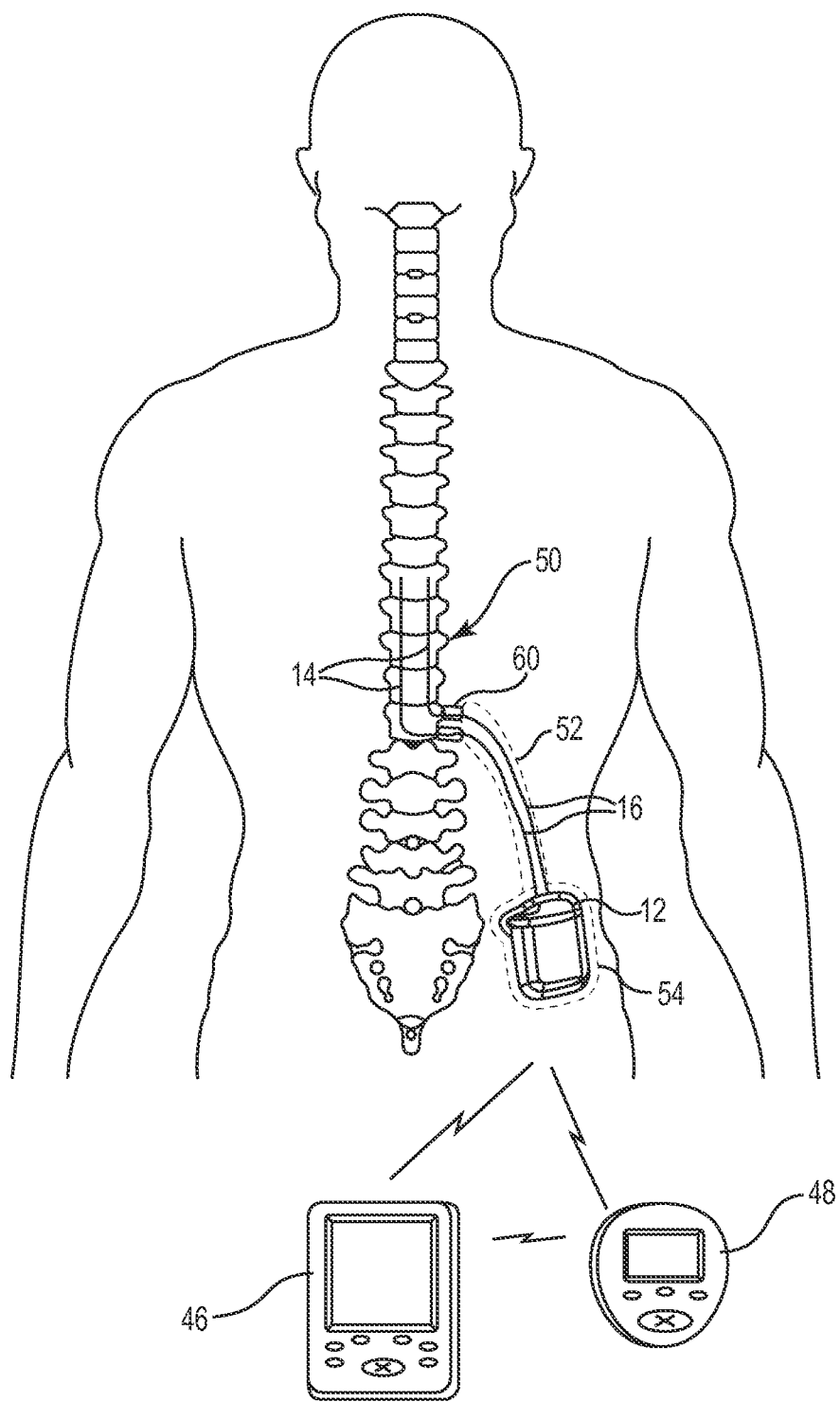
FIG. 3 is an alternate illustration of the environment for an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 3. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector 22 of the implantable pulse generator 12, since different manufacturers use different connectors at the ends of their stimulation leads and are not always compatible with the connector 22.

As illustrated in FIG. 3, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 46, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

FIG. 3 also illustrates a general environmental that may benefit from use of a tunneling tool in accordance with an embodiment of the present disclosure. Since the implantable pulse generator 12 is located remotely from target location 50 for therapy, the therapy delivery element 14 and/or the extension lead 16 is typically routed through a pathway 52 subcutaneously formed along the torso of the patient to a subcutaneous pocket 54 where the implantable pulse generator 12 is located. As used hereinafter, "lead" and "lead extension" may be used interchangeably, unless context indicates otherwise.

The therapy delivery elements 14 are typically fixed in place near the location selected by the clinician using the present suture anchors 60. The suture anchors 60 can be positioned on the therapy delivery element 14 in a wide variety of locations and orientations to accommodate individual anatomical differences and the preferences of the clinician. The suture anchors 60 may then be affixed to tissue using fasteners, such as for example, one or more sutures, staples, screws, or other fixation devices. The tissue to which the suture anchors 60 are affixed may include subcutaneous fascia layer, bone, or some other type of tissue. Securing the suture anchors 60 to tissue in this manner prevents or reduces the chance that the therapy delivery element 14 will become dislodged or will migrate in an undesired manner.

Figure 4A:
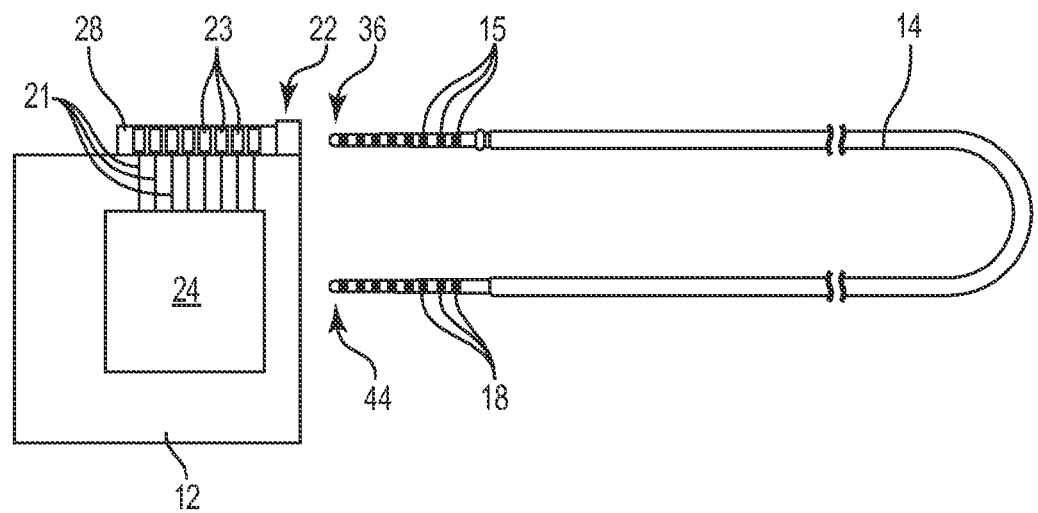
FIG. 4A is a schematic illustration of an implantable pulse generator and a therapy delivery element in accordance with an embodiment of the present disclosure.

FIG. 4A illustrates the therapy delivery element 14 including one or more electrical contacts 15 at the proximal end 36, and one or more electrodes 18 at the distal end 44. The contacts 15 and electrodes 18 are electrically coupled via insulated wires running through the therapy delivery element 14. Proximal end 36 of the therapy delivery element 14 is electrically and mechanically coupled to implantable pulse generator 12 by the connector assembly 22. In the embodiment illustrated in FIGS. 4A and 4B, the therapy delivery element 14 forms a medical electrical lead.

The connector assembly 22 includes a plurality of discrete contacts 23 located in the housing 28 that electrically couple contact rings 15 on the proximal end of the therapy delivery element 14. The discrete contacts 23 are electrically coupled to circuitry 24 in the implantable pulse generator 12 by conductive members 21. Each contact ring 15 is electrically coupled to one or more of the electrodes 18 located at the distal end 44 of the therapy delivery element 14. Consequently, the implantable pulse generator 12 can be configures to independently deliver electrical impulses to each of the electrodes 18.

Figure 4B:
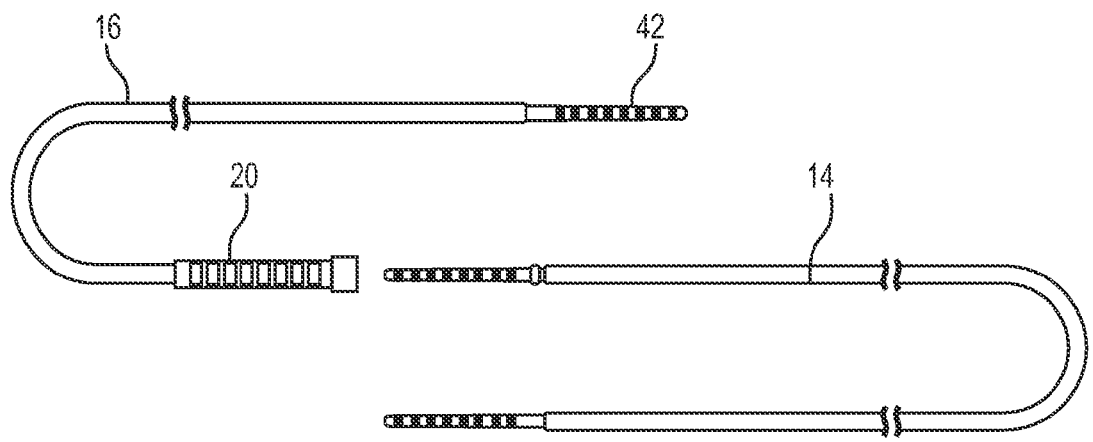
FIG. 4B is a schematic illustration of a lead extension and a therapy delivery element in accordance with an embodiment of the present disclosure.

Alternatively, the therapy delivery element 14 can be coupled to the implantable pulse generator 12 through one or more lead extensions 16, as illustrated in FIG. 4B. The connector 20 at the distal end 38 of the lead extension 16 preferably includes a plurality of the contacts 23 configured in a manner similar to the connector assembly 22.

FIGS. 5A and 5B illustrate a stylet/lead assembly 70 including the therapy delivery element 14 in accordance with an embodiment of the present disclosure. The term stylet refers to a tool inserted into the lumen of a therapy delivery element, such as a neurostimulation lead, to stiffen the lead body and to facilitate its insertion to a target tissue site.

In the illustrated embodiment, stylet 72 includes stylet wire 74 attached to handle 76. The stylet wire 74 has a diameter smaller than lumen 78 in the lead body 86 of the therapy delivery element 14. Length 80 is typically the same, or slightly greater than, length 82 of the lumen 78 so the distal end 84 of the stylet wire 74 preferably reaches distal end 85 of the therapy delivery element 14. The distal end 85 of the therapy delivery element is typically sealed, so the length 82 of the lumen 78 is less than the length of the therapy delivery element 14. In use, distal end 84 of the stylet wire 74 is inserted in lumen 78 of the therapy delivery element 14 to create the stylet/lead assembly 70.

Conventional stylet wires for the SCS application are typically made of stainless steel or tungsten. While super-elastic materials may provide excellent kink resistance, they can also feature poor resistance to buckling forces and torque. Consequently, a stylet wire 74 made from these materials alone may not be suitable for use for SCS therapy delivery elements. Stylet wires manufactured from combinations of linear and super-elastic materials have been evaluated, as disclosed in U.S. Pat. Nos. 6,214,016; 6,168,571; 5,238,004; 6,270,496 and 5,957,966, which are hereby incorporated by reference.

Figure 6A:
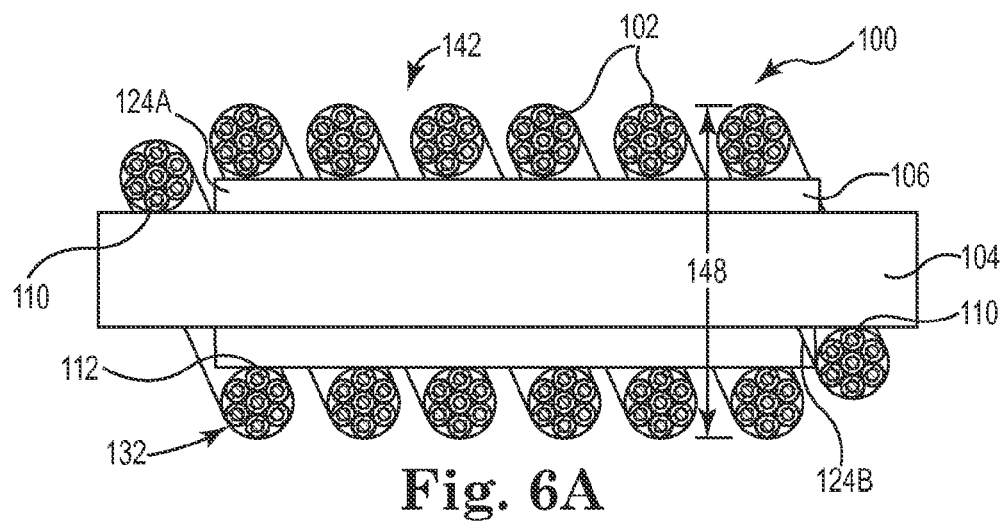
FIGS. 6A through 6D illustrate a method of making a lead body with a dynamic coil in accordance with an embodiment of the present disclosure.
Figure 6B:
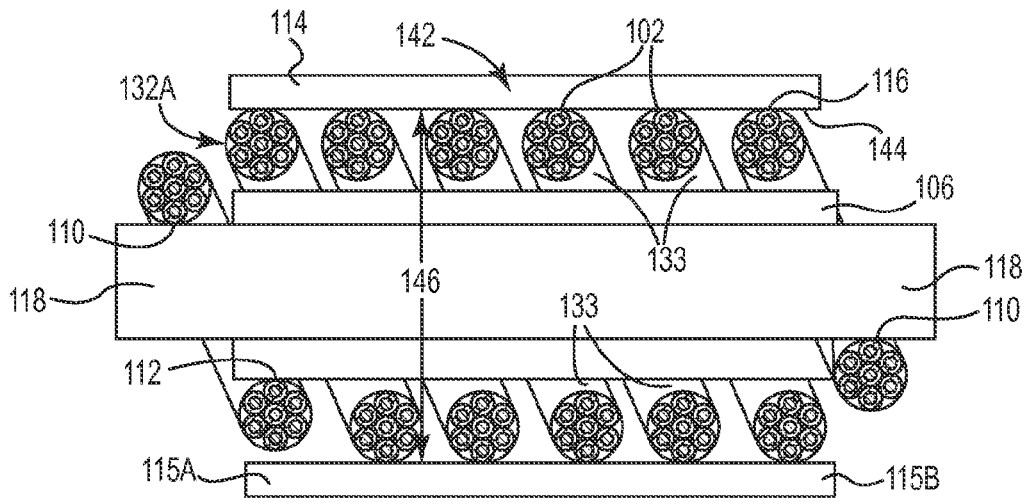
Figure 6C:
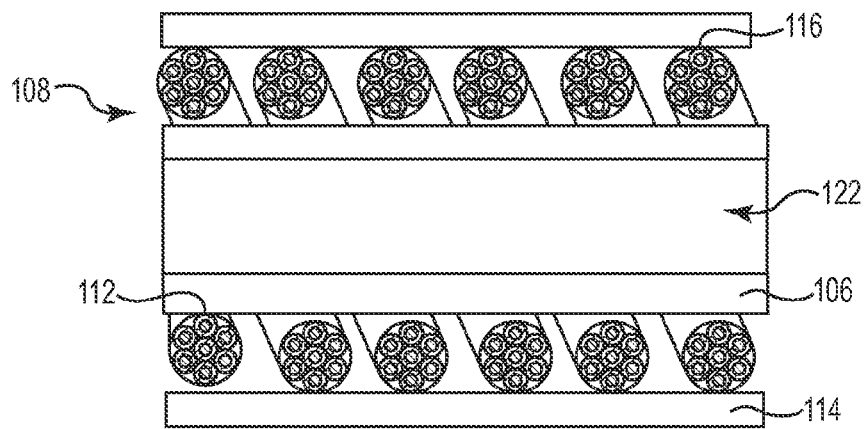

FIGS. 6A-6D illustrate one embodiment of a method for making a dynamic coil 100 for a therapy delivery element 14, such as a stimulation lead or an extension. One or more conductors 102 are coiled around a core or mandrel 104 to form the dynamic coil 100. Stress on the conductors during the winding procedure is preferably at or below the yield point to minimize or prevent plastic deformation of the conductors 102. In particular, the conductors 102 are wrapped loosely around the mandrel 104, rather than "formed" to the mandrel 104, without plastically deforming the conductors 102. Any stress on the conductors 102 during coiling is preferably below the elastic limit 141 of the stress-strain curve for the particular conductors being used (see e.g., FIG. 7).

As a result, the conductors 102 have substantially no memory of the coiled configuration 132. Mechanical restraints, discussed below, are required to maintain the conductors 102 in the coiled configuration 132. If the mechanical restrains are removed the conductors 102 tend to unravel. Residual deformation of the conductors 102 typically assumes the form of waviness in the wires or loose loops with diameters greater than diameter 148 of the dynamic coil 100. As used herein, "dynamic coil" refers to one or more conductors coiled at or below a yield point that are retained in a coiled configuration by mechanical restraints.

Figure 6D:
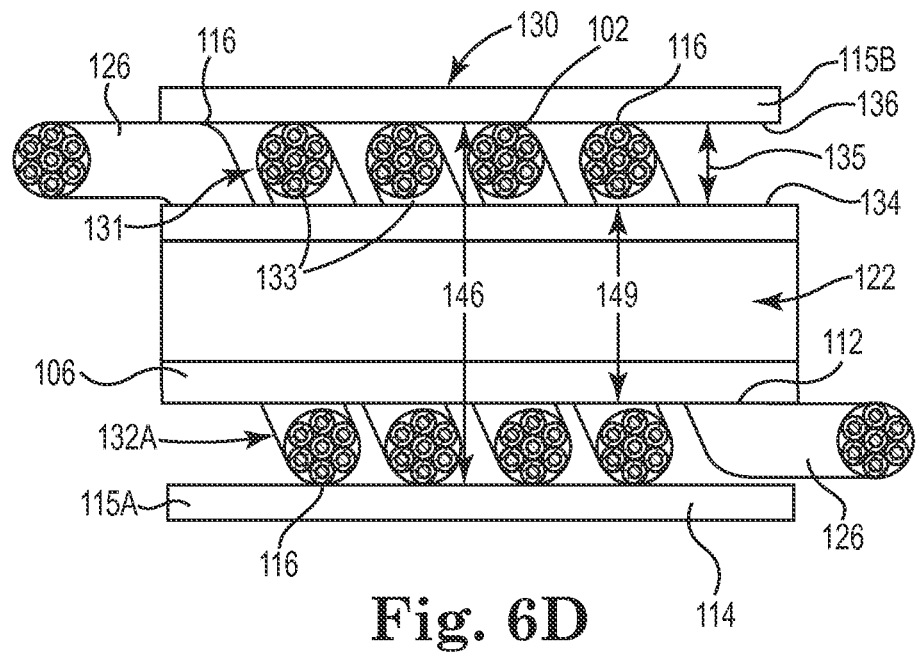
Figure 7:
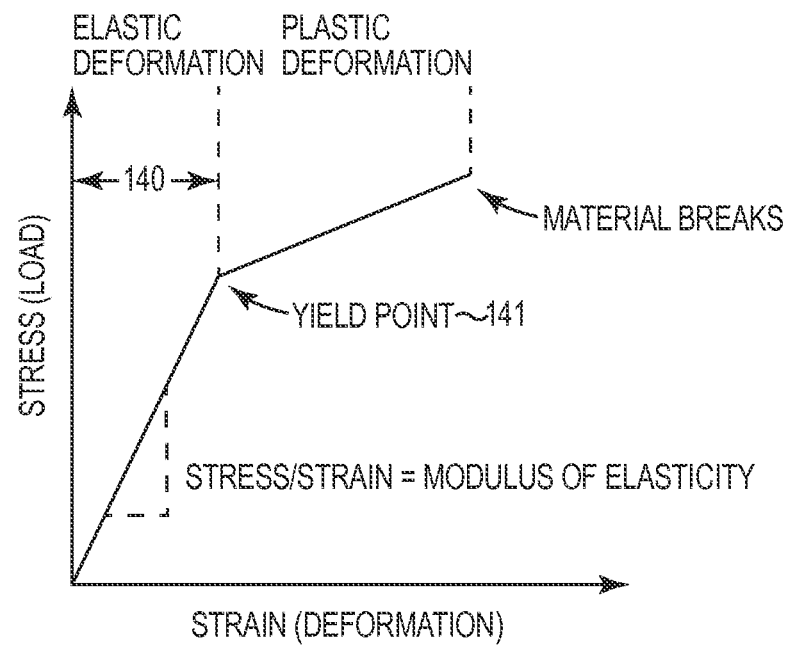
FIG. 7 is an exemplary stress strain curve illustrating a feature of a dynamic coil in accordance with an embodiment of the present disclosure.

In the illustrated embodiment, the mandrel 104 includes an optional inner tubular structure 106 that assists in incorporating the dynamic coil 100 into assembly 108 (see FIG. 6D). The inner tubular structure 106 also facilitates removal of the mandrel 104 later in the process. The inner tubular structure 106 is preferably elastic in at least the longitudinal direction to permit the dynamic coil 100 to elongate.

The inner tubular structure 106 can be a variety of structures, such as for example, a stylet coil, a braid, an extruded tube, or a combination thereof. The inner tubular structure 106 can be made from metal, polymeric materials, or a combination thereof. In alternate embodiments discussed herein the sleeve acts as the mandrel and the mandrel 104 is not required. In another embodiment, the functions of the mandrel 104 and the inner tubular structure 106 are combined into an elastic core member around which the dynamic coil 100 is formed. The elastic core member can be formed with or without a central lumen. For example, a lead extension does not require a lumen and the dynamic coil 100 can be formed around a solid elastic cylindrical member.

As illustrated in FIG. 6A, the conductors 102 are preferably secured to the mandrel 104 at locations 110 and to the inner tubular structure 106 at location 112, such as by adhesive bonding, solvent bonding, thermal welding, ultrasonic welding, and the like. The attachment location 112 is located primarily near distal end 124A of the inner tubular structure 106 so that the conductors 102 in center region 142 are free to shift and move relative to the inner tubular structure 106 during elongation or bending of the lead body 100.

The attachment locations 110 to the mandrel 104 provide temporary mechanical restraints that serve to secure the conductors 102 in coiled configuration 132 during subsequent processing of the present lead body 100. Without the attachment locations 110, 112 the conductors 102 would unravel.

As illustrated in FIG. 6B, outer tubular structure 114 is positioned around the conductors 102. The outer tubular structure 114 is a covering layer that can be molded in place or preformed and slid over the conductors 102 using various methods known in the art. The conductors 102 are optionally secured to the outer tubular structure 114, such as near proximal end 115B at locations 116. In another embodiment, the outer tubular structure 114 compressively restrains the conductors 102 against the inner tubular structure 106 to form attachment location 112, 116.

Inside diameter 146 of the outer tubular structure 114 is greater than the outside diameter 148 of the conductors 102 in the coiled configuration 132 (see FIG. 6A). Since the attachment locations 110, 112, 116 are located at the distal and proximal ends 115A, 115B, the conductors 102 are not constrained in the center region 142. As a result, the elastically coiled conductors 102 are free to expand to the inside surface 144 of the outer tubular structure 114 to an expanded coiled configuration 132A. If the conductors 102 are plastically deformed during the coiling process, little or no expansion will occur.

The expanded coiled configuration 132A includes space 133 between the conductors 102 and the inner tubular structure 106. During elongation of the dynamic coil 100, the conductors 102 neck-down to close the space 133. Although FIG. 6B illustrates the space 133 as generally symmetrical around the inner tubular structure 106, in practice the dynamic coil 100 is free to shift in the space 133.

As illustrated in FIG. 6C, distal portions 118 of the mandrel 102 have been cut-off and removed from the assembly 108, thereby eliminating the attachments 110 to the mandrel 102. At this point the remaining portion of the mandrel 104 can be removed from the assembly 108, exposing lumen 122.

In the illustrated embodiment, the conductors 102 are retained in the expanded coiled configuration 132A by mechanical restrains at attachment locations 112 and 116. The attachment locations 112, 116 can be formed to either the inner tubular structure 106 or the outer tubular structure 114.

As illustrated in FIG. 6D, free ends 126 of the conductors 102 are released from the assembly 108 and extend beyond the distal and proximal ends 115A, 115B of the outer tubular structure 114. Because winding occurs within the elastic range of the stress-strain characteristics of the conductors 102 shown in FIG. 7, the free ends 126 relax to a generally straight configuration.

The free ends 126 facilitate attachment of the individual conductors 102 to the electrodes 18 and electrical contacts 15 (see FIG. 4A). In one embodiment, the attachment locations 112, 116 are eliminated and the mechanical restraints on the dynamical coil 100 are solely the attachments to the electrodes 18 and the electrical contacts 15.

The resulting lead body 130 includes a helically or spirally wound coil 131 of conductors 102 constrained by outer tubular structure 114 in an expanded coiled configuration 132A. In one embodiment, the inner tubular structure 106 remains part of the lead body 130 so the helical or spiral coil 131 is retained in gap 135 between the opposing surfaces 134, 136. The helical coil 131 typically expands within the gap 135 to the limit of the insider surface 136 of the outer tubular structure 114.

The percentage elongation of the dynamic coil 100 is determined, in part, by the size of the space 133. The space 133 is a function of the gap 135 between inside diameter 146 of the outer tubular structure 114, the outside diameter 149 of the inner tubular structure 106, and the diameter of the conductors 102.

During elongation the conductors 102 tend to neck-down and compressively engage the inner tubular structure 106. In one embodiment, the inner tubular structure 106 is elastically deformable, thereby increasing the percent elongation of the dynamic coil 100.

The inner tubular structure 106 also serves to define the lumen 122 that can receive a stylet, such as the stylet 72 illustrated in FIGS. 5A and 5B. In this embodiment, the inner tubular structure 106 serves as a stylet coil that protects the conductors 102 from damage during insertion and removes of the stylet 72.

In an alternate embodiment, the inner tubular structure 106 is removed and the outer tubular structure 114 is the sole structure retaining the conductors 102 in the expanded coiled configuration 132A. Since the conductors 102 are not plastically deformed to a permanent coil, the conductors 102 tend to press against inside surface 136 of the outer tubular structure 114. Attachment locations 116 with the outer tubular structure 114 serve to retain the conductors 102 within the outer tubular structure 114 in the expanded coiled configuration 132A.

The present helical or spiral coil 131 has the same or better flex fatigue properties to a straight conductor or cable, yet functions like a conventional coil when loaded axially. Flex fatigue life is generally measured by bending the sample around a known radius and measuring the number of cycles until failure, as measured according to European Standard EN 45502-2-1:2003, Section 23.3, which is hereby incorporated by reference. According to this standard, the test fixture rotates the lead body +/−90 degrees from vertical around bending radius of 6 mm+/−0.1 mm for a minimum of 47,000 cycles at a rate of 2 Hz. The conductors are then evaluated for fracture.

Flex fatigue occurs when a material is subjected to repeated loading and unloading. If the loads are above a certain threshold, microscopic cracks will begin to form at the material. Eventually a crack will reach a critical size, and the structure will suddenly fracture. Failure is essentially probabilistic and damage is cumulative. The number of cycles required for failure varies between homogeneous material samples and materials to not recover when rested.

Two lead bodies with four conductors were subject to about 3 million bending cycles according to European Standard EN 45502-2-1:2003, Section 23.3. The first lead body was configured as a dynamic coil in accordance with the present disclosure and passed the test without failure. The second lead body was configured with four longitudinally oriented conductors as is well known in the art and experienced one conductor failure.

The greater the applied stress during loading and unloading of a material, the shorter the flex fatigue life. The opposite is also true. Since the present coil 131 is configured with little or no latent stress on the conductors 102, the flex fatigue life of the conductors 102 is increased. The pitch and the number of the conductors 102 do not appear to have much impact on flex fatigue life of the present lead body 130.

The electrical conductors 102 can include a single conductive element, a plurality of conductive wires, or a combination thereof. As illustrated in FIG. 8, one or more of the electrical conductors 102 optionally include a plurality of un-insulated conductive wires 150a-150g (collectively "150") twisted in a ropelike configuration 152. Insulator 154 surrounds the conductive wires 150 to form one of the electrical conductors 102, also referred to a cable. The wires 150 are preferably not rigidly connected together, but rather, only contact one another and can move with respect to one another within certain limits.

In the illustrated embodiment, the six outer wires 150a-150f are uniformly distributed around the center wire 150g. The outer wires 150a-150f are preferably composites including a core 156 of a first material and a covering 158 of a second material. The core 156 preferably has greater electrical conductivity than the covering 158 and the covering 158 preferably has a greater breaking strength and increase biocompatibility than the core 156. For example, the core 156 can be silver or copper and the covering 158 can be a nickel-cobalt-chromium-molybdenum alloy, such as for example, MP35N.

The center wire 150g is preferably constructed from a material with a greater breaking strength than the six outer wires 150a-150f. The center wire 150g can optionally be constructed from a non-conductive material, such as for example a monofilament. In one embodiment, the center wire 150g is constructed from the same material as the lead body 128. Alternatively, the center wire 150g can be one of a variety of alloys, such as the CoNiCrMoWFe alloy (standard ASTM F 563-78) supplied under the commercial name Syntacoben by Institut Straumann AG, Switzerland; the CoCrFeNi alloy supplied under the commercial name Elgiloy by Elgin National Watch Co., U.S.A.; stainless steel, such as the Fe, Cr, Ni, Mo containing steel (standards ISO 5832/1; ASTM F 138-76) commercially available under the designation 316 L; or a variety of other materials disclosed in U.S. Pat. No. 4,640,983 (Comte), which is hereby incorporated by reference.

In one embodiment, bending stress, or flexure stress, varies with position throughout the cross section of the wires 150. Stress is substantially zero at the center of the wires 150, but increases with distance from the center. Since the maximum stress occurs at the surface of the wires 150, using a composite material with the strongest material on the covering 158 provides a significant advantage by allowing greater stress without permanent deformation. Since minimal stress occurs in the core 156 of the wire 150, it is less important that the core material be strong.

According to one embodiment, the conductors 102 are the cable 152 illustrated in FIG. 8 with seven 0.005 inch diameter, silver core MP35N conductor 150 arranged in the illustrated 1×7 configuration and covered with an ETFE (ethylene tetrafluoroethylene) coating 154. The cables 152 are wrapped around the mandrel 104 with an outside diameter of about 0.016 inches using winding tensions or forces that range between about 1 ounce to about 2 ounces. Little or no permanent deformation of conductors 150 occurs during the coiling process. The conductors 150 typically resume a relaxed configuration when mechanical constraints (e.g., 110 and 112) are removed.

The winding machine pitch setting was about 0.09 inches to about 0.15 inches, which translates to about 9 to about 7 revolution per inch (depend on whether 8 or 12 cables 152 are used). The resulting lead body described above exhibited a percent elongation that is dependent on a number of variable, including the number of conductors, winding pitch, and the gap between the outside diameter of the inner stylet coil and the inside diameter of the outer tubing.

As noted above, current multi-conductor coils permit essentially zero elongation. Lead bodies made according to the present disclosure, however, provide multiple conductors that meet the bending radius and flex fatigue requirements set forth in European Standard EN 45502-2-1:2003, Section 23.3, while providing a percent elongation suitable for an implantable conductor assembly.

Figure 13:
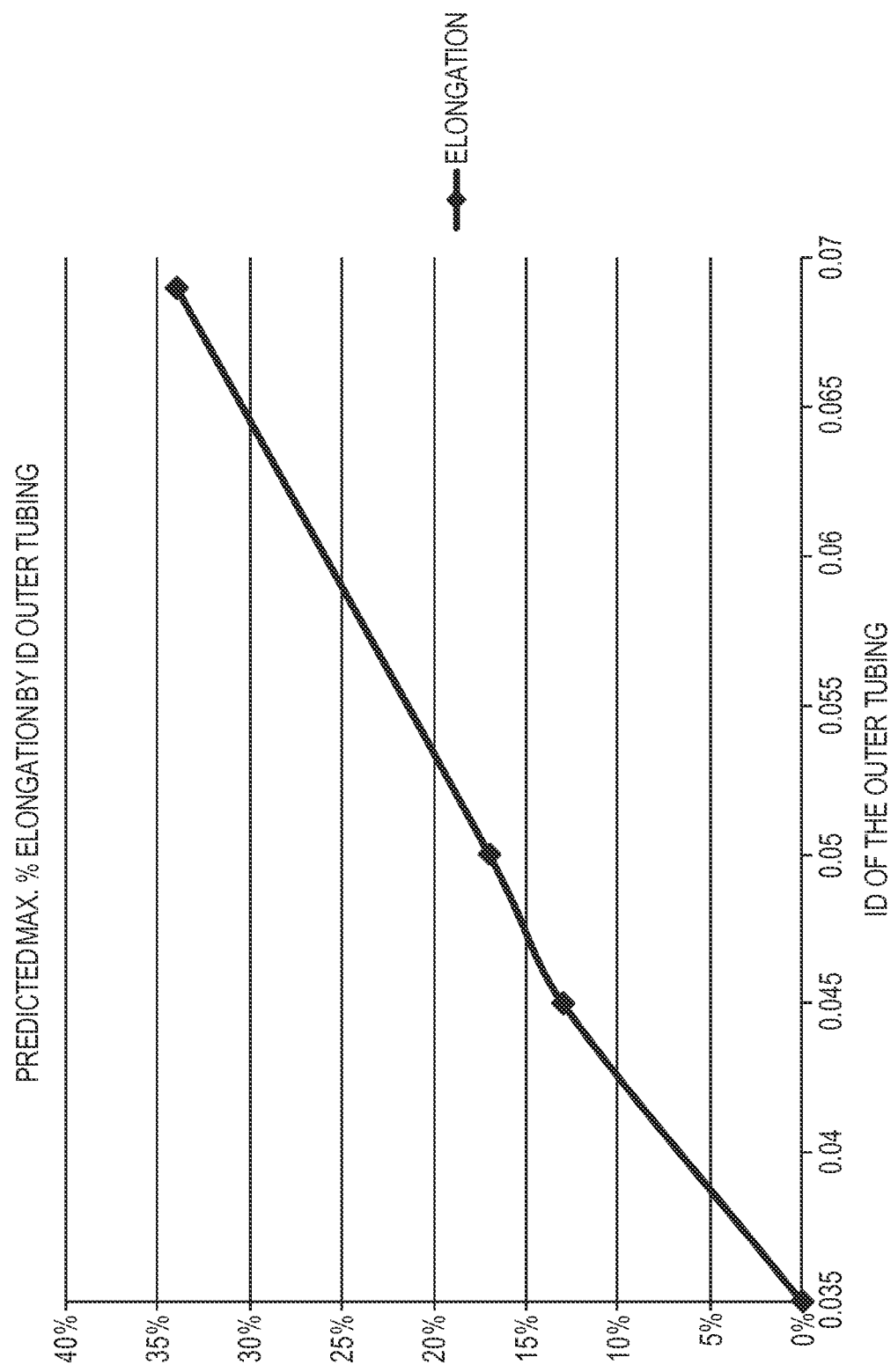
FIG. 13 is a graph illustrating the percent elongation of the present lead body as a function of inside diameter of the outer tubular structure.

FIG. 13 illustrates the impact on percent elongation as a function of the gap between the inner tubular structure and the outer tubular structure. The stylet coil was formed from round wire having a diameter of about 0.014 inches and had an outer diameter of about 0.024 inches. Twelve conductors were helically wound around the stylet coil in a generally side-by-side configuration at a pitch of about 0.07. Each conductor include seven 0.005 inch diameter, silver core MP35N wires arranged in the illustrated 1×7 configuration and covered with an ETFE (ethylene tetrafluoroethylene) coating. Table 1 below lists (i) the inside diameter of the outer tubing, (ii) the gap between the outside diameter of the inner tubing and the inside diameter of the outer tubing, and (iii) the corresponding percent elongation is set forth in Table 1 below.

TABLE 1

| Outer Tubing ID (Inches) | Gap (Inches) | Percent Elongation |
| --- | --- | --- |
| 0.035 | 0.011 | 0% |
| 0.045 | 0.021 | 13% |
| 0.05 | 0.026 | 17% |
| 0.069 | 0.045 | 34% |

For example, increasing the gap from about 0.021 inches to about 0.026 inches (an increase of about 24%), increases the percent elongation by about 31%. Similarly, increasing the gap from about 0.026 inches to about 0.045 inches (an increase of about 74%), increases the percent elongation by about 100%.

As set forth in Table 2 below, the tighter the winding pitch of the conductors the greater the percentage elongation.

TABLE 2

| Pitch (Inches) | Outer Tube ID (Inches) | Percent Elongation |
| --- | --- | --- |
| 0.06 | 0.045 | 13% |
| 0.15 | 0.045 | 2% |
| 0.06 | 0.069 | 34% |
| 0.15 | 0.069 | 17% |

For example, outer tubing having an ID of about 0.045 inches, decreasing the pitch about 60% increases the percent elongation about 550%. Similarly, for outer tubing having an ID of about 0.069 inches, decreasing the pitch about 60% increases the percent elongation about 100%

The present disclosure provides a lead body with anywhere from 1 to up to 12 conductors/cables helically coiled at a pitch in a range of between about 0.07 inches and about 0.15 inches located in a gap between two generally concentric tubular structures in a range of between about 0.015 inches to about 0.045 inches or between about 0.020 inches to about 0.045 inches that exhibits a percent elongation in a range between about 10 percent to about 35 percent, and between about 15 percent to about 30 percent, and between about 20 percent and about 25 percent. The present lead body has an outside diameter of less than about 0.080 inches, and less than about 0.060 inches and meets the bending radius and flex fatigue requirements set forth in European Standard EN 45502-2-1:2003, Section 23.3.

The present disclosure provides a lead body with anywhere from 1 to up to 16 conductors/cables helically coiled at a pitch in a range of between about 0.07 inches and about 0.15 inches located in a gap between two generally concentric tubular structures in a range of between about 0.015 inches to about 0.045 inches or between about 0.020 inches to about 0.045 inches that exhibits a percent elongation in a range between about 10 percent to about 25 percent, and between about 15 percent to about 20 percent.

FIG. 9 illustrates an alternate dynamic coil 160 for a stimulation lead in accordance with an embodiment of the present disclosure. One or more conductors 162 are coiled around a stylet coil 164 to form the dynamic coil 160. In the illustrated embodiment, the core 162 is formed from one or more individual wires 172 deformed to create a self-supporting coil structure 174.

Little or no stress or load is placed on the conductors 162 during winding to minimize plastic or permanent deformation. As a result, the conductors expand to engage inner surface 176 of the outer tubing 164. Gap 178 is formed between the helical or spiral coil 166 and the stylet coil 164.

During elongation the coil 166 necks down to close the gap 178 until the conductors 162 engage the stylet coil 164. Free ends 170 of the conductors 162 extend beyond the tubing 164 in a relaxed configuration.

Figure 10:
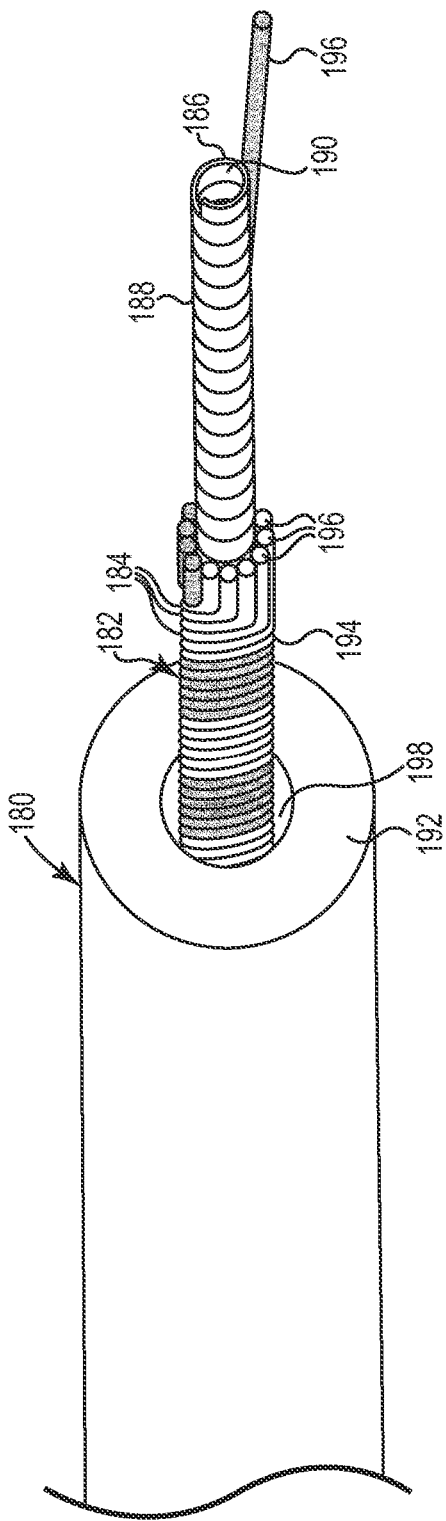
FIG. 10 illustrates an alternate dynamic coil with a flat wire core in accordance with an embodiment of the present disclosure.

FIG. 10 is a cut-away view of a lead body 180 with a dynamic coil 182 having a plurality of generally co-planar conductor 184 in accordance with an embodiment of the present disclosure. Flat wire 186 is coiled to form inner coil 188 (also referred to as a stylet coil) around which the conductors 184 are wound. The inner coil 188 includes lumen 190 sized to receive a stylet (see e.g., FIG. 5A). In this embodiment, the inner coil 188 acts as the mandrel and a separate mandrel is not required. In one embodiment, the inner coil 188 is coiled clockwise, and the conductors are coiled counter-clockwise.

Tubing 192 surrounds the dynamic coil 182. Gap 198 exists between the tubing 192 and the conductors 184. In the illustrated embodiment, the inner coil 188 is bonded to the conductors 184 only at attachment location 194. As a result, the dynamic coil 182 expands to the limits of the gap 198 in the expanded coiled configuration (see e.g., FIG. 6D). In another embodiment, distal ends of the tubing 192 is heat shrunk onto the conductors 184, such as at the attachment location 194, to compressively secures the conductors 184 against the inner coil 188. Free ends 196 of the conductors 184 unravel and extend beyond the lead body 180 to facilitate attachment to electrical connectors and electrodes (see e.g., FIG. 1).

Figure 11:
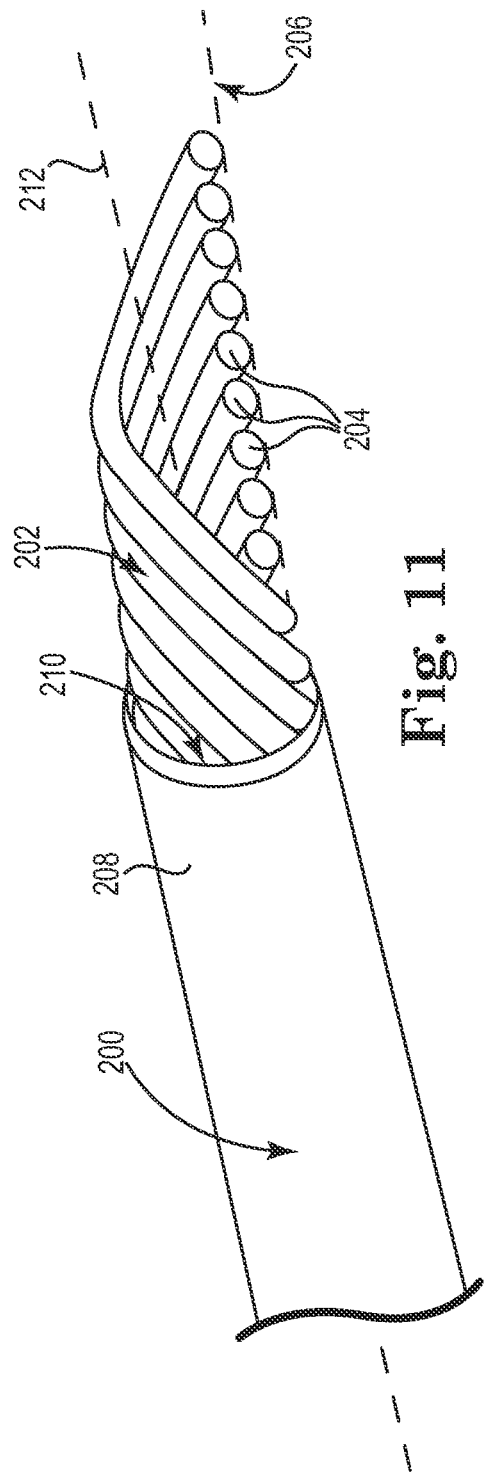
FIG. 11 illustrates an alternate dynamic coil without a core in accordance with an embodiment of the present disclosure.

FIG. 11 illustrates a lead body 200 with a dynamic coil 202 having a plurality of conductors 204 have portions thereof all located in a single plane 206 in accordance with one embodiment of the present disclosure. The dynamic coil 202 is located in the lumen 210 of the tubular structure 208, without the use of an inner tubular structure. The dynamic coil 202 is attached to the tubular structure 208 near proximal and distal ends thereof, as discussed herein. The absence of an inner tubular structure permits the dynamic coil 202 to neck down until the conductors 204 are generally oriented along longitudinal axis 212 of the tubular structure 208, increasing the percent elongation of the lead body 200.

As noted above, the number or pitch of the conductors 204 has little or no impact on the flex fatigue life of the lead body 200. Consequently, the lead body 200 can accommodate twelve or more conductors 204 with little or no impact on profile height, thickness, stiffness, or electrical resistance. For example, the lead body 200 can have for example, sixteen or twenty four conductors 202 with the same or similar overall diameter as a conventional lead body with eight to twelve conductors.

Figure 12:
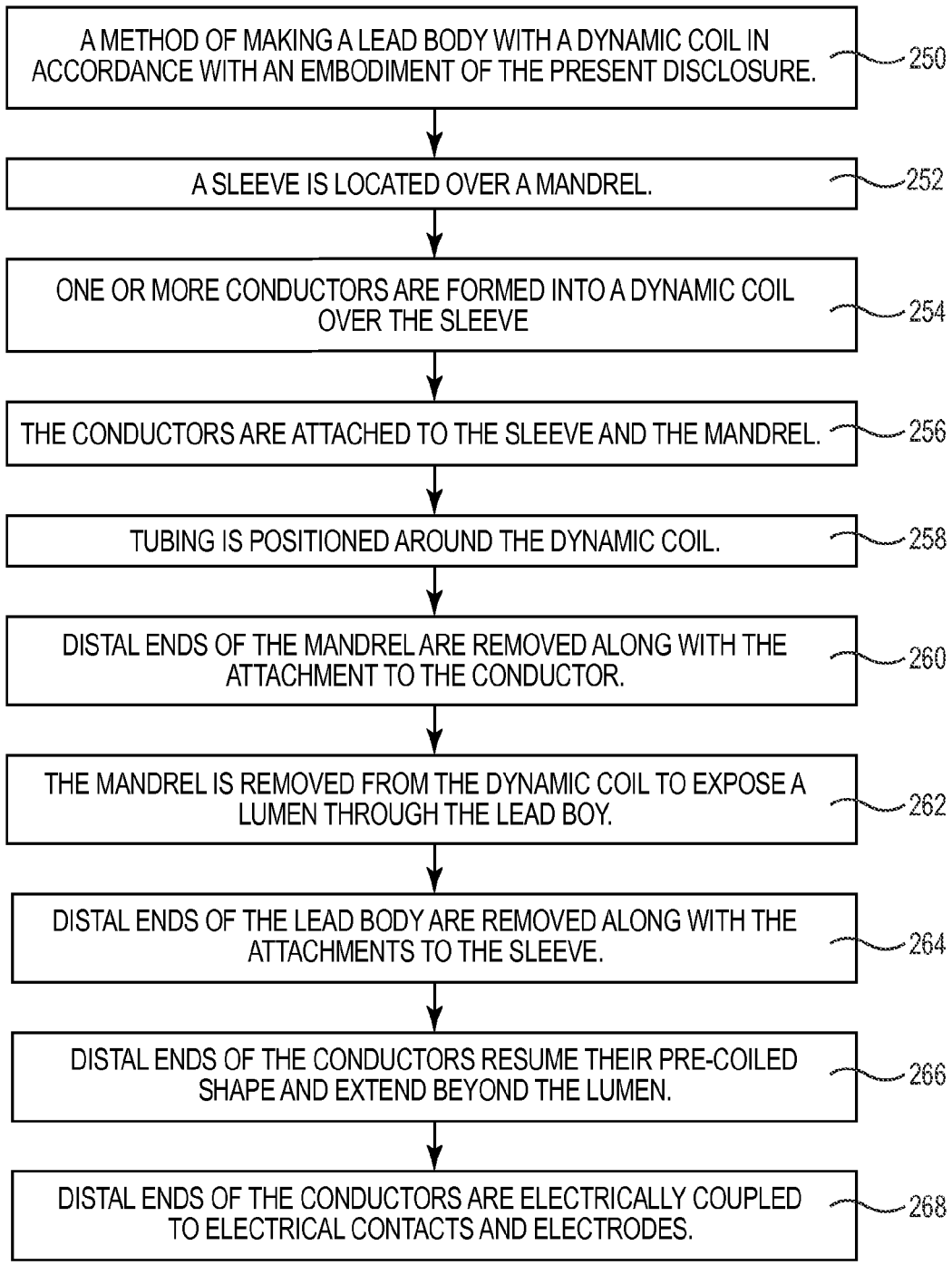
FIG. 12 is a flow chart of a method of making a lead body with a dynamic coil in accordance with an embodiment of the present disclosure.

FIG. 12 is a flow chart of a method of making a lead body with a dynamic coil in accordance with an embodiment of the present disclosure (250). A sleeve is located over a mandrel (252). One or more conductors are formed into a dynamic coil over the sleeve (254). The conductors are attached to the sleeve and the mandrel (256). Tubing is positioned around the dynamic coil (258). Distal ends of the mandrel are removed along with the attachment to the conductor (260). The mandrel is removed from the dynamic coil to expose a lumen through the lead body (262). Distal ends of the lead body are removed along with the attachments to the sleeve (264). Free ends of the conductors resume their relaxed shape and extend beyond the lumen (266). Free ends of the conductors are electrically coupled to electrical contacts and electrodes (268). In an alternate embodiment the free ends of the conductors are electrically coupled to electrical contacts and a connector as part of an extension.

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. An implantable biomedical conductor assembly configured for at least partial insertion in a living body, comprising:
   an inner tubular structure;
   an outer tubular structure generally surrounding the inner tubular structure so that a gap of less than or equal to 0.030 inches exists between the inner tubular structure and the outer tubular structure; and
   a dynamic coil located in the gap, the dynamic coil comprising a plurality of insulated conductors coiled below a yield point of the insulated conductors, the dynamic coil being permitted to expand within the gap to engage an inner surface of the outer tubular structure in an expanded coiled configuration, at least one mechanical restraint being located at or near each of a distal end and a proximal end of the outer tubular structure to retain the dynamic coil between at least portions of the inner tubular structure and the outer tubular structure in the coiled configuration below the yield point of the insulated conductors;
   wherein free ends of the insulated conductors extend beyond the proximal and distal ends of the outer tubular structure and are attached to corresponding connectors and electrodes, the free ends being relaxed from the coiled configuration into a substantially straight configuration.

2. The implantable conductor assembly of claim 1, wherein at least a portion of the dynamic coil unravels if one or more of the mechanical restraints is removed, and any unraveled coils comprise a diameter greater than a diameter of the dynamic coil in the expanded coiled configuration.

3. The implantable conductor assembly of claim 1, wherein at least one of the mechanical restraints comprises attachment locations that secure the insulated conductors to at least one of the inner tubular structure or the outer tubular structure at or near at least one of the proximal end or the distal end of the outer tubular structure.

4. The implantable conductor assembly of claim 1, wherein at least one of the mechanical restraints comprises free ends of the insulated conductors attached to at least one of the electrodes or the connectors.

5. The implantable conductor assembly of claim 1, wherein the coiled configuration comprises a plurality of insulated conductors having portions thereof arranged in a single plane.

6. The implantable conductor assembly of claim 1, wherein the expanded coiled configuration comprises up to twelve insulated conductors, the implantable conductor assembly including a percent elongation in a range between about 10 percent to about 35 percent.

7. The implantable conductor assembly of claim 1, wherein the expanded coiled configuration comprises up to sixteen insulated conductors, the implantable conductor assembly including a percent elongation in a range between about 10 percent to about 25 percent.

8. The implantable conductor assembly of claim 1, wherein an outside diameter of the implantable conductor assembly is less than or equal to 0.080 inches.

9. The implantable conductor assembly of claim 1, wherein the inner tubular structure comprises one of a stylet coil, a braided structure, extruded tube, or a combination thereof.

10. The implantable conductor assembly of claim 1, wherein the inner tubular structure comprises a lumen sized to receive a stylet wire.

11. The implantable conductor assembly of claim 1, wherein the coiled configuration comprises up to twelve coiled conductors and meets the bending radius and flex fatigue requirements set forth in European Standard EN 45502-2-1:2003, Section 23.3.

12. The implantable conductor assembly of claim 1, wherein the implantable conductor assembly comprises a portion of a medical electrical lead or a fluid delivery device.

13. An implantable biomedical conductor assembly configured for at least partial insertion in a living body, comprising:
   a tubular structure comprising a lumen; and
   a dynamic coil located in the lumen, the dynamic coil including a plurality of insulated conductors coiled below a yield point of the insulated conductors, the dynamic coil being permitted to expand within the tubular structure to engage an inner surface of the lumen in an expanded coiled configuration, at least one mechanical restraint being located at each of a distal end and a proximal end of the tubular structure to retain the dynamic coil in the lumen in the coiled configuration below the yield point of the insulated conductors;
   wherein free ends of the insulated conductors extend beyond proximal and distal ends of the tubular structure to facilitate attachment to connectors and electrodes, respectively, the free ends being relaxed from the coiled configuration into a substantially straight configuration.

14. The implantable conductor assembly of claim 13, wherein at least a portion of the dynamic coil unravels if one or more of the at least one mechanical restraint is removed, and any unraveled coils include a diameter greater than a diameter of the dynamic coil in the expanded coiled configuration.

15. The implantable conductor assembly of claim 13, wherein at least one of the at least one mechanical restraint includes attachment locations configured to secure the insulated conductors to the tubular structure at or near at least one of the proximal end or the distal end of the tubular structure.

16. The implantable conductor assembly of claim 13, wherein at least one of the at least one mechanical restraint includes free ends of the insulated conductors attached to at least one of the electrodes or the connectors.

17. The implantable conductor assembly of claim 13, comprising an inner tubular structure disposed within the tubular structure, the inner tubular structure including at least one of a stylet coil, a braided structure, or an extruded tube.

18. The implantable conductor assembly of claim 17, wherein the tubular structure and the inner tubular structure are separated by a gap of less than or equal to 0.030 inches.

19. An implantable biomedical conductor assembly configured for at least partial insertion in a living body, comprising:
   an inner tubular structure;
   an outer tubular structure generally disposed around the inner tubular structure, wherein the inner tubular structure is separated from the outer tubular structure by a gap; and
   a dynamic coil disposed within the gap, the dynamic coil including a plurality of insulated conductors coiled below a yield point of the conductors, the dynamic coil being permitted to expand within the gap to engage an inner surface of the outer tubular structure in an expanded coiled configuration, at least one mechanical restraint being located at or near each of a distal end and a proximal end of the outer tubular structure to retain the dynamic coil between at least portions of the inner tubular structure and the outer tubular structure in the coiled configuration below the yield point of the insulated conductors, wherein each of the insulated conductors includes two free ends, one free end extending beyond the proximal end of the outer tubular structure and the other free end extending beyond the distal end of the outer tubular structure, each of the free ends being relaxed from the coiled configuration into a substantially straight configuration and configured to be attached to an electrode or a connector.

20. The implantable conductor assembly of claim 19, wherein at least one of the at least one mechanical restraint includes attachment locations configured to secure the insulated conductors to the outer tubular structure at or near at least one of the proximal end or the distal end of the outer tubular structure.

21. The implantable conductor assembly of claim 19, wherein the inner tubular structure includes a lumen sized to receive a stylet wire, and wherein the gap between the inner tubular structure and the outer tubular structure is 0.030 inches or less.

\* \* \* \* \*